United States Patent [19]

Kumai et al.

[11] Patent Number: 5,072,062

[45] Date of Patent: Dec. 10, 1991

[54] BROMINATION METHOD

[75] Inventors: Seisaku Kumai, Fujisawa; Akihiro Wada, Yokohama, both of Japan

[73] Assignee: Asahi Glass Company, Ltd., Tokyo, Japan

[21] Appl. No.: 680,077

[22] Filed: Apr. 3, 1991

[30] Foreign Application Priority Data

Apr. 3, 1990 [JP] Japan .................................. 1-87465

[51] Int. Cl.$^5$ ............................................. C07C 17/20
[52] U.S. Cl. .................................................. 570/170
[58] Field of Search ........................ 570/170, 255, 153

[56] References Cited

U.S. PATENT DOCUMENTS 4,794,200  12/1988  Tordeux et al. .

FOREIGN PATENT DOCUMENTS 0184033  9/1985  Japan .

Primary Examiner—Alan Siegel
Attorney, Agent, or Firm—Oblon, Spivak, McClelland, Maier & Neustadt

[57] ABSTRACT

A method for brominating a perfluoroalkyl iodide or a perfluoroalkylene diiodide, which comprises reacting a perfluoroalkyl iodide or a perfluoroalkylene diiodide with a brominating agent in a gas phase to obtain a perfluoroalkyl bromide or a perfluoroalkylene dibromide.

10 Claims, No Drawings

BROMINATION METHOD

The present invention relates to a method for producing a perfluoroalkyl bromide or a perfluoroalkylene dibromide which is useful as e.g. an intermediate for pharmaceutical products.

Heretofore, the following methods are known for the production of a perfluoroalkyl bromide or a perfluoroalkylene dibromide.

1. A method wherein a perfluoroalkyl iodide or a perfluoroalkylene diiodide is used as a starting material, and it is brominated by bromine in a liquid phase in the presence of radical initiator (Japanese Unexamined Patent Publication No. 184033/1985).

2. A method wherein a perfluoroalkylsulfonyl chloride is used as a starting material, and it is brominated by hydrogen bromide in a liquid phase to obtain a perfluoroalkyl bromide.

The method wherein a perfluoroalkyl iodide or a perfluoroalkylene diiodide is used as the starting material, presents a low yield and is hardly applicable as an industrial method. Besides, it requires a radical initiator, which adds to the cost. Therefore, this method is not suitable for industrial production.

On the other hand, the method wherein a perfluoroalkylsulfonyl chloride is used as the starting material, presents a high yield, but the starting material perfluoroalkylsulfonyl chloride is hardly available and expensive. Therefore, this method is also not suitable for industrial production.

It is an object of the present invention to solve the problems of e.g. a low yield and use of expensive raw material, inherent to the prior art and to provide a method for producing a perfluoroalkyl bromide or a perfluoroalkylene dibromide in good yield and at low cost on an industrial scale.

The present invention provides a novel method for producing a perfluoroalkyl bromide or a perfluoroalkylene dibromide, wherein a perfluoroalkyl iodide or a perfluoroalkylene diiodide is used as the starting material, and it is brominated in a gas phase by means of a brominating agent.

Now, the present invention will be described in detail with reference the preferred embodiments.

The method of the present invention may be represented by the following reaction scheme.

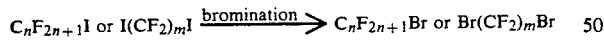

$C_nF_{2n+1}I$ or $I(CF_2)_mI$ $\xrightarrow{\text{bromination}}$ $C_nF_{2n+1}Br$ or $Br(CF_2)_mBr$ In the above formulas, each of n and m is an integer of from 2 to 16, and in the application as a contrast medium or as an artificial blood, each of n and m is usually an integer of from 4 to 12, preferably from 6 to 10.

The starting material perfluoroalkyl iodide or perfluoroalkylene diiodide is a compound which is readily available on an industrial scale. The bromination reaction can simply be conducted by reacting the starting material with a brominating agent in a gas phase. The reaction can be conducted at a reaction temperature of from 150° to 500° C., preferably from 250° to 500° C., more preferably from 300° to 400° C., for a retention time of from 2 to 360 seconds, preferably from 5 to 60 seconds. As the brominating agent, a compound capable of liberating bromine, such as IBr or IBr$_3$, may be employed as well as bromine. It is particularly preferred to employ bromine. The brominating agent is employed in an amount of from 0.1 to 10 mols, preferably from 0.5 to 1.5 mols, per mol of the starting material. When the starting material is a perfluoroalkyl bromide, bromine is used preferably in an amount of from 0.5 to 1.5 mols per mol of the starting material. When the starting material is a perfluoroalkylene dibromide, bromine is used preferably in an amount of from 1 to 3 mols per of the starting material. At the time of bromination, the atmosphere may be diluted with a gas inert to the reaction such as nitrogen or a perfluoroalkane. When a perfluoroalkyl iodide which is hardly vaporized because the carbon number of the perfluoroalkyl group is large, is used as the starting material, it is possible to facilitate the vaporization by diluting it with a gas inert to the reaction. Further, such dilution serves to remove the heat of reaction. The diluting ratio is preferably such that the diluting gas is within a range of from 0.01 to 10 mols per mol of the perfluoroalkyl iodide. Further, a method may be employed wherein the starting material is preliminarily dissolved in a solvent inert to the reaction.

However, from the viewpoint of the productivity as well as from the viewpoint of the costs for raw materials, it is preferred to minimize extra additives and to react the starting material and bromine without using any additive as far as possible.

It has been found that in this reaction iodine in the perfluoroalkyl iodide or in the perfluoroalkylene diiodide is substituted by bromine and liberated as single substance iodine. This liberated iodine can be reused as a useful resource.

For this reaction, highly corrosive bromine is employed, and likewise highly corrosive iodine is liberated. However, by using a corrosion resistant material such as Inconel or hastelloy as the material for the reactor, it is possible to conduct the production on an industrial scale with no substantial corrosion.

A perfluoroalkyl bromide is useful as a pharmaceutical or its intermediate, or as a surfactant or its intermediate. Particularly, perfluorooctyl bromide is useful as a contrast medium for e.g. stomach, or for an artificial blood. A perfluorooctyl bromide may be used as it is or as dispersed in water by means of an emulsifier such as a lecithin.

Now, the present invention will be described in further detail with reference to Examples. However, it should be understood that the present invention is by no means restricted by such specific Examples.

EXAMPLE 1

273 g (0.5 mol) of perfluorooctyl iodide was continuously supplied to a vaporizer made of Inconel and vaporized over a period of 20 minutes and then supplied to a reactor together with a small amount of nitrogen. The molar ratio of perfluorooctyl iodide to nitrogen was 1:0.25. On the other hand, bromine was continuously supplied to a vaporizer made of glass and vaporized, and then supplied to the reactor in a similar manner. Here, the molar ratio of the perfluorooctyl iodide to bromine was 1:0.7. A mixture of the above gas and the bromine gas was passed through a reaction tube made of Inconel having a inner diameter of 27 mm and a length of 1,000 mm and maintained at a temperature of 350° C. by a salt bath furnace, and the liquid cooled and condensed at the outlet was analyzed by gas chromatography, whereby the conversion of the perfluorooctyl iodide was 99%, and the selectivity for perfluorooctyl bromide was 99%.

EXAMPLE 2

The reaction was conducted in the same manner as in Example 1 except that molar ratio of the perfluorooctyl iodide to bromide was changed to 1:0.5, whereby the conversion of the perfluorooctyl iodide was 93%, and the selectivity for perfluorooctyl bromide was 99%.

EXAMPLE 3

The reaction was conducted in the same manner as in Example 1 except that 223 g (0.5 mol) of perfluorohexyl iodide was used instead of 273 g (0.5 mol) of perfluorooctyl iodide, whereby the conversion of perfluorohexyl iodide was 99%, and the selectivity for perfluorohexyl bromide was 99%.

EXAMPLE 4

The reaction was conducted in the same manner as in Example 1 except that 323 g (0.5 mol) of perfluorodecanyl iodide was used instead of 273 g (0.5 mol) of perfluorooctyl iodide, whereby the conversion of perfluorodecanyl iodide was 97%, and the selectivity for perfluorodecanyl bromide was 98%.

EXAMPLE 5

The reaction was conducted in the same manner as in Example 1 except that 327 g (0.5 mol) of perfluorooctyl1,8-diiodide was continuously supplied over a period of 27 minutes instead of 273 g (0.5 mol) of perfluorooctyl iodide, and the molar ratio of the perfluorooctyl-1,8-diiodide to bromine was adjusted to 1:1.4, whereby the conversion of the perfluorooctyl-1,8-diiodide was 90%, and the selectivity for perfluorooctyl-1,8-dibromide was 92%, and the selectivity for perfluorooctyl-1-iodo-8-bromide was 5%.

COMPARATIVE EXAMPLE 1

1 mol of perfluorooctyl iodide and 0.7 mol of bromine were supplied to an Erlenmeyer flask made of glass and reacted in a liquid phase at 60° C. for 10 hours under reflux of bromine. The reaction product thereby obtained was analyzed by gas chromatography, whereby the conversion of the perfluorooctyl iodide was less than 1%, and no perfluorooctyl bromide was detected.

As described in the foregoing, according to the present invention, it is possible to obtain a perfluoroalkyl bromide or a perfluoroalkylene dibromide in good yield and at a low cost on an industrial scale.

We claim:

1. A method for brominating a perfluoroalkyl iodide, which comprises reacting a perfluoroalkyl iodide with bromine IBr or IBr$_3$ in a gas phase at a temperature of from 150° to 500° C. to obtain a perfluoroalkyl bromide.

2. The method according to claim 1, wherein the carbon number of the perfluoroalkyl group of each of the perfluoroalkyl iodide and the perfluoroalkyl bromide is from 6 to 10.

3. The method according to claim 1, wherein the perfluoroalkyl iodide is perfluorooctyl iodide, and the perfluoroalkyl bromide is perfluorooctyl bromide.

4. The method according to claim 1, wherein the reaction ratio of the perfluoroalkyl iodide and the brominating agent is such that the brominating agent is selected within a range of from 0.1 to 10 mols per mol of the perfluoroalkyl iodide.

5. The method according to claim 1, wherein the reaction ratio of the perfluoroalkyl iodide and bromine is such that bromine is selected within a range of from 0.5 to 1.5 mols per moi of the perfluoroalkyl iodide.

6. A method for brominating a perfluoroalkylene diiodide, which comprises reacting a perfluoroalkylene diiodide with bromine in a gas at a temperature of from 150° to 500° C. phase to obtain a perfluoroalkylene dibromide.

7. The method according to claim 6, wherein the carbon number of the perfluoroalkylene group of each of the perfluoroalkylene diiodide and the perfluoroalkylene dibromide is form 6 to 10.

8. The method according to claim 6, wherein the perfluoroalkylene diiodide is perfluorooctyl-1,8-diiodide, and the perfluoroalkylene dibromide is perfluorooctyl-1,8-dibromide.

9. The method according to claim 6, wherein the reaction ratio of the perfluoroalkylene diiodide and the brominating agent is such that the brominating agent is selected within a range of from 0.1 to 10 mols per mol of the perfluoroalkylene diiodide.

10. The method according to claim 6, wherein the reaction ratio of the perfluoroalkylene diiodide and bromine is such that bromine is selected within a range of from 1 to 3 mols per mol of the perfluoroalkylene diiodide.

* * * * *